US007960347B2

(12) United States Patent
Hammarstrom et al.

(10) Patent No.: US 7,960,347 B2
(45) Date of Patent: Jun. 14, 2011

(54) MATRIX PROTEIN COMPOSITIONS FOR INDUCTION OF APOPTOSIS

(75) Inventors: Lars Hammarstrom, Djursholm (SE); Stale Petter Lyngstadaas, Nesoddtangen (NO); Stina Gestrelius, Lund (SE)

(73) Assignee: Institut Straumann AG, Basel (CH)

( * ) Notice: Subject to any disclaimer, the term of this patent is extended or adjusted under 35 U.S.C. 154(b) by 0 days.

(21) Appl. No.: 12/760,074

(22) Filed: Apr. 14, 2010

(65) Prior Publication Data

US 2010/0234298 A1   Sep. 16, 2010

Related U.S. Application Data

(63) Continuation of application No. 10/878,380, filed on Jun. 29, 2004, now abandoned, which is a continuation of application No. 09/521,742, filed on Mar. 9, 2000, now abandoned.

(60) Provisional application No. 60/134,813, filed on May 19, 1999.

(30) Foreign Application Priority Data

Mar. 10, 1999   (DK) .................................. 1999 00336

(51) Int. Cl.
*A01N 61/00* (2006.01)
*A61K 31/00* (2006.01)
*A61K 38/00* (2006.01)

(52) U.S. Cl. ........... 514/18.9; 514/1; 514/1.1; 514/19.2; 514/19.3

(58) Field of Classification Search ................ 514/1, 1.1, 514/18.9, 19.2, 19.3
See application file for complete search history.

(56) References Cited

U.S. PATENT DOCUMENTS

| 4,672,032 | A  | 6/1987 | Slavkin et al.     |
| 6,503,539 | B2 | 1/2003 | Gestrelius et al.  |

FOREIGN PATENT DOCUMENTS

| EP | 0263086 A1    | 4/1988 |
| EP | 0337967 A2    | 10/1989 |
| WO | WO 97/02730 A2 | 1/1997 |
| WO | WO 99/43344 A2 | 9/1999 |

OTHER PUBLICATIONS

Scully, Robert E. Pathology of Ovarian Cancer Precursors. Journal of Cellular Biochemistry, Supplement 23: 208-218, 1995.*
Pre-appeal Examination Report dated Sep. 7, 2010 in corresponding JP Application No. 2000-603685, with English language translation.
"Critical Reviews in Oral Biology & Medicine" Proteinases in Developing Dental Enamel, J.D. Bartlett and J.P. Simmer, Crit. Rev. Oral Biol. Med. 1999, pp. 425-441.
Vitale, M. et al., "Fibronectin is Required to Prevent Thyroid Cell Apoptosis through an Integrin-Mediated Adhesion Mechanism", Endocrinol. Metab. 83 (10), 1998, pp. 3673-3680.
Zhang, Z. et al., "The alpha 5 beta 1 integrin supports survival of cells on fibronectin and up-regulates Bcl-2 expression", Proc. Natl. Acad. Sci. USA 92 (13), 1995, pp. 6161-6165.
Kim, H. J. et al., "Integrin mediation of type II cell adherence to provisional matrix proteins", Am. J. Physiol. 271 (2 pt. 1), 1996, pp. L277-L286.
McGill, G. et al., "Loss of Matrix Adhesion Triggers Rapid Transformation-Selective Apoptosis in Fibroblasts", J. Cell Biol. 138 (4), 1997, pp. 901-911.
Mason, M. D. et al., "Adhesion molecules in melanoma—more than just superglue?", J. R. Soc. Med. 89 (7), 1996, pp. 393-395.
Buckley, C.D. et al., "RGD peptides induce apoptosis by direct caspase-3 activation", Nature 397, Feb. 1999, pp. 534-539.
Gestrelius et al., "In vitro studies on periodontal ligament cells and enamel matrix derivative", J. Clinical Periodontology, 24:685 (1997).
Lyngstadaas et al., "Autocrine growth factors in human periodontal ligament cells cultured on enamel matrix derivative", J. Clinical Periodontology, 28:181 (2001).
Kawase et al., "Cytostatic action of enamel matrix derivative (EMDOGAIN) on human oral sqamous cell carcinoma-derived SCC25 epithelial cells", J. Periodont. Res. 35:291 (2000).
Cancer: Principles and Practice of Oncology, 5th edition, (Editors, Devita, Jr. et al. Lippincott-Raven Publishers, pp. 1433-1437, 1997).
Ruddon, Raymond W. Cancer Biology, third edition. New York: Oxford University Press, 1995.
Gura, T., "Systems for Identifying Drugs Are Often Faulty", Science 278: 1041 and 1042, Nov. 7, 1997.

* cited by examiner

*Primary Examiner* — Alana M Harris
(74) *Attorney, Agent, or Firm* — Rissman Hendricks & Oliverio, LLP

(57) ABSTRACT

Enamel matrix, enamel matrix derivatives and/or enamel matrix proteins or peptides may be used as therapeutic or prophylactic agents for inducing programmed cell death (apoptosis), in particular in the treatment or prevention of cancer or malignant or benign neoplasms.

15 Claims, 3 Drawing Sheets

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Gly Glu Ala
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Thr Lys Gly
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Lys Gly Glu
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Lys Gly Glu
1

MATRIX PROTEIN COMPOSITIONS FOR INDUCTION OF APOPTOSIS

This application is a continuation application of U.S. application Ser. No. 10/878,380, filed Jun. 29, 2004, which is a continuation of U.S. application Ser. No. 09/521,742, filed Mar. 9, 2000, which claims the benefit of priority of U.S. Provisional Application Ser. No. 60/134,813, filed May 19, 1999, and Denmark Application No. PA 1999 00336, filed Mar. 10, 1999, the disclosures of which are incorporated herein in their entirety by reference.

SEQUENCE LISTING

The instant application contains a Sequence Listing which has been submitted via EFS-Web and is hereby incorporated by reference in its entirety. Said ASCII copy, created on May 25, 2010, is named S7505US2.txt and is 1,198 bytes in size.

FIELD OF INVENTION

The present invention relates to the use of enamel matrix, enamel matrix derivatives and/or enamel matrix proteins or peptides as therapeutic or prophylactic agents for inducing programmed cell death.

BACKGROUND OF THE INVENTION

Enamel matrix proteins such as those present in enamel matrix are best known as precursors of dental enamel. Enamel proteins and enamel matrix derivatives have previously been described in the patent literature to induce hard tissue formation (i.e. enamel formation, cf. U.S. Pat. No. 4,672,032 (Slavkin)) or binding between hard tissues (EP-B-0 337 967 and EP-B-0 263 086). In recent animal studies using enamel matrix proteins for regeneration of tooth attachment, it has been observed that the regeneration and healing progresses with minimal signs of epithelial interference. This is in contrast to all other regenerative therapies of the periodontium where epithelial downgrowth from the oral cavity into the lesion is a common complication. To investigate possible restrictive effects of enamel matrix proteins on epithelial cell growth, epithelial cells were cultured in the presence of enamel matrix proteins.

SUMMARY OF THE INVENTION

It has surprisingly been found that epithelial cancer cells (HeLa cells) which are not ameloblasts and which are not found in the periodontal environment and which do not participate in tooth development undergo apoptosis (programmed or induced cell death) when cultured in the presence of enamel matrix, enamel matrix derivatives and/or enamel matrix proteins (in the following collectively termed "active enamel substance"). Accordingly, the present invention relates to the use of a preparation of an active enamel substance for the preparation of a pharmaceutical composition for the induction of apoptosis.

In another aspect, the invention relates to the use of a preparation of an active enamel substance for the preparation of a pharmaceutical composition for the prevention or treatment of malignant or benign neoplasms.

In a further aspect, the invention relates to the use of a preparation of an active enamel substance for the preparation of a pharmaceutical composition for the prevention or treatment of cancer.

In a still further aspect, the invention relates to the use of a preparation of an active enamel substance for the preparation of a pharmaceutical composition for the (selective) induction of apoptosis in neoplastic cells.

In a still further aspect, the present invention relates to method for inducing apoptosis in neoplastic cells, the method comprising applying an effective amount of an active enamel substance at or on neoplastic cells.

Apoptosis (programmed or induced cell death) is involved in the focal elimination of certain cells during normal development and in the turnover of cells in healthy adult tissues. Examples where apoptosis has been found to be involved are in organogenesis during embryonic life, e.g. the separation of digits during limb development, cusp and root formation during tooth development, elimination of worn-out cells in the small intestine, and clonal elimination of lymphocytes that might otherwise react with "self" antigens.

Recent evidence suggests that apoptosis may be equally important in the understanding of carcinogenesis and for developing novel therapies for different neoplastic diseases. Thus, it has been shown that apoptosis is involved in preventing genome instability from developing in cells in which the cell cycle has been perturbed, and it is associated with injurious stimuli such as therapeutic irradiation and cytotoxic drugs used to treat malignant neoplasms.

Apoptosis is a gene-regulated process involving the synthesis of some proteins that promote apoptosis and others that protect against it. The presence of the tumour suppressor gene p53 is responsible for the initiation of apoptosis as a result of cell injury, in particular injury caused by DNA double-stranded breaks. In human cancer treatment, this is extremely important because tumour cells from which p53 is absent do not undergo apoptosis when exposed to ionising radiation. In addition, lack of p53 is likely to result in the survival of cells in which DNA mutations have occurred and thus to increase the risk of development of cancer. Certain cells that have been deprived of growth promoting factors or whose growth have been arrested with cytotoxic drugs are rendered susceptible to apoptosis by expression of the proto-oncogene c-myc. This gene encodes an essential part of the proliferative machinery of the cell, and deregulation of the expression of this gene is implicated in most neoplasms. Certain gene products protect cells from apoptosis. Examples of such gene products include those of the bcl-2 gene, the proto-oncogene c-abl and the LMP-1 gene of the Epstein-Barr virus.

A number of different pathways for induction of apoptosis have been demonstrated. Gamma irradiation acts directly on the chromosomes by causing DNA strand breaks. Certain hormones such as glucocorticoids induce apoptosis in thymocytes, probably via a glucocorticoid receptor complex. A third induction pathway is via a direct contact with the plasma membrane of the target cells. An example of this is the effect of granzyme B which is released as part of the interaction of cytotoxic T-cells with a target cell.

In epithelial cells, apoptosis has been found to take place when cell adhesion to extracellular matrix by means of fibronectin and other extracellular proteins is blocked. In an immortalised thyroid cell line, it appeared that adhesion, spreading and cytoskeleton organisation were dependent on integrin-fibronectin interaction. It has been shown that cells become apoptotic when peptides containing the RGD (Arg-Gly-Asp) motif inhibit binding of fibronectin to integrin receptors (cf. M. Vitale et al., J. Clin. Endocrinol. Metab. 83 (10), 1998, pp. 3673-3680). Similar findings have been reported for normal cells by, e.g., Z Zhang et al., Proc. Natl. Acad. Sci. USA 92 (13), 1995, pp. 6161-6165; H J Kim et al., Am. J. Physiol. 271 (2 pt. 1), 1996, pp. L277-286; G McGill et al., J. Cell Biol. 138 (4), 1997, pp. 901-911. Inhibition of adhesion resulting in cell death not only happens to normal (non-transformed) cells, but has also been shown for melanoma cells. Thus, M D Mason at al., J. R. Soc. Med. 89 (7), 1996, pp. 393-395, reported that loss of integrin-mediated signalling induced apoptosis in melanoma cells within 3 days of treatment with a peptide containing the RGD motif blocking the alpha v beta 3 integrin. Furthermore, it has been shown that the RDG motif is an integrin-recognition motif, and that peptides containing RDG induce apoptosis by activation of caspase-3 which is an enzyme that participates in a cascade resulting in disassembly of the cell (cf. C D Buckley et al., Nature 397, February 1999, pp. 534-539).

Without wishing to be limited to any particular hypothesis, it is currently believed that the active enamel substance may exert its apoptosis inducing effect either by binding to cell surface receptors in an analogous manner to RDG so as to block the site needed for cellular adhesion to extracellular matrix, or by binding to cells surface structures such as CD44 or integrins, thereby directly activating caspase 3 and triggering the apoptotic pathway described by Buckley et al., supra.

In developing teeth, the enamel is formed by a layer of epithelial cells called ameloblasts. These, in turn, are supported by another layer of epithelial cells providing the ameloblasts with growth factors and nutrients required for their continued existence and function. The ameloblasts synthesize and secrete enamel matrix proteins which, together with mineral and water, consitute the enamel matrix which is an early developmental stage of dental enamel. Enamel matrix proteins are mainly present during the secretory stage of enamel formation. After their initial deposition, they are gradually degraded and then lost as enamel development progresses. Also, during enamel development, apoptosis is observed in epithelial cells close to the enamel matrix. This apoptotic event is preceded by translocation of enamel matrix degradation products from the developing enamel into the enamel organ that is composed of epithelial cells. The active enamel substance observed to be useful in the present invention is composed of a number of proteins and peptides including such degradation products. These observations are also supported by studies of guinea pig molars showing that processing of enamel proteins is linked to the reduction of the number of surrounding epithelial cells (cf. Example 1 below).

DETAILED DESCRIPTION OF THE INVENTION

Apoptosis has attracted considerable interest for the potential treatment of cancers and neoplasms. The present inventors surprisingly observed that when human epithelial cancer cells (HeLa cells) were cultured in the presence of the active enamel substance they underwent apoptosis (vide Example 2 below). By way of comparison, human connective tissue cells (fibroblasts) cultured under similar conditions in the presence of the active enamel substance were stimulated as to growth. Based on these results, the present inventors believe that the active enamel substance may be used for the (selective) induction of apoptosis in neoplastic cells, specifically in the treatment, e.g. topical treatment, of certain types of cancer and benign, semimalignant (i.e. locally invasive) or malignant neoplasms.

It is currently believed that the active enamel substance may be particularly beneficial for use in the treatment of epithelially derived cancers or neoplasms, as the results currently available appear to show that the active enamel substance exerts its apoptotic effect specifically on epithelial cells. In the use according to the present invention, it is therefore preferred to apply the active enamel substance topically at or on affected tissue comprising a substantial proportion of epithelial cells. In particular, such tissue comprises skin or mucosal tissue. Mucosal tissue which may advantageously be treated with the active enamel substance in accordance with the invention comprises any tissue which presents a suitable surface available for topical application of the active enamel substance, either naturally or following surgical incision. Examples of such mucosal surfaces are oral, gastrointestinal, respiratory tract (e.g. lung), cervical or abdominal mucosa.

Other tissues comprising a significant proportion of epithelial cells are glandular tissues, e.g. mammary gland, pancreas, liver, thyroid gland, bladder, ovary, prostate, sweat gland, salivary gland or pituitary gland tissue.

It has been found, however, that cancer cells derived from other tissues than epithelial or mucosal tissue or other tissues comprising a significant number of epithelial cells also exhibit a marked increase in apoptosis when treated with the preparation of active enamel substance according to the invention (vide Example 3 below). The present invention therefore extends to the use of a preparation of the active enamel substance in the treatment of cancers or neoplasms in tissue such as bone or muscle tissue.

On surgical removal of a tumour, it is important to reduce the risk that tumour cells migrate from the site of surgery to invade another part of the body. In a specific embodiment of the present invention, the active enamel substance is therefore applied at or on a tumour site before, during or after surgical removal of a tumour or neoplastic tissue to substantially reduce the risk of postsurgical metastasis and/or to prevent recurrence of the tumour at the site of surgery. In particular, it is envisaged that the preparation of active enamel substance may be applied for adjuvant cancer therapy, e.g. in conjunction with conventional radiation therapy. It is currently believed that such adjuvant therapy using the active enamel substance may both reduce the risk of tumour cell migration (i.e. metastasis) in accordance with the present findings and contribute to the healing of wounds often resulting from radiation therapy as the active enamel substance has also been found to exhibit wound healing properties (vide for instance WO 99/43344).

Apart from the treatment of cancer or neoplastic tissue, it is contemplated that the active enamel substance may be used for the prophylaxis or treatment of warts, in particular warts resulting from viral infection, e.g. papilloma or condyloma.

Enamel Matrix, Enamel Matrix Derivatives and Enamel Matrix Proteins

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is for example fish skin.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, optionally followed by freeze-drying. Enzymes may be deactivated by treatment with heat or solvents, in which case the derivatives may be stored in liquid form without freeze-drying.

In the present context, enamel matrix derivatives are derivatives of enamel matrix which include one or several of enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix protein derivatives also include enamel matrix related polypeptides or proteins. The polypeptides or proteins may be bound to a suitable biodegradable carrier molecule, such as polyamino acids or polysaccharides, or combinations thereof. Furthermore, the term enamel matrix derivatives also encompasses synthetic analogous substances.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Daltons or more. Small proteins are called peptides or oligopeptides.

Enamel matrix proteins are proteins which normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general such proteins have a molecular weight below 120,000 daltons and include amelogenins, non-amelogenins, proline-rich non-amelogenins, amelins (ameloblastin, sheathlin) and tuftelins.

Examples of proteins for use according to the invention are amelogenins, proline-rich non-amelogenins, tuftelin, tuft proteins, serum proteins, salivary proteins, amelin, enamelin, ameloblastin, sheathlin, and derivatives thereof, and mixtures thereof. A preparation containing an active enamel substance for use according to the invention may also contain at least two of the aforementioned proteinaceous substances. A commercial product comprising amelogenins and possibly other enamel matrix proteins is marketed as EMDOGAIN® (Biora AB).

In general, the major proteins of an enamel matrix are known as amelogenins. They constitute about 90% w/w of the matrix proteins. The remaining 10% w/w includes proline-rich non-amelogenins, tuftelin, tuft proteins, serum proteins and at least one salivary protein; however, other proteins may also be present such as, e.g., amelin (ameloblastin, sheathlin) which have been identified in association with enamel matrix. Furthermore, the various proteins may be synthesized and/or processed in several different sizes (i.e. different molecular weights). Thus, the dominating proteins in enamel matrix, amelogenins, have been found to exist in several different sizes which together form supramolecular aggregates. They are markedly hydrophobic substances which under physiologically conditions form aggregates. They may carry or be carriers for other proteins or peptides.

Other protein substances are also contemplated to be suitable for use according to the present invention. Examples include proteins such as proline-rich proteins and polyproline. Other examples of substances which are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS Page electrophoresis. As indicated above, epithelial cells associated with ameloblasts are believed to be induced to undergo apoptosis by degradation products migrating from the enamel matrix during dental enamel development. Such degradation products, which generally have a molecular weight between about 3 kDa and 25 kDa, such as between 5 kDa and 20 kDa, may be particularly effective for use according to the present invention.

The proteins for use according to the invention are normally presented in the form of a preparation, wherein the protein content of the active enamel substance in the preparation is in a range of from about 0.05% w/w to 100% w/w such as, e.g., about 5-99% w/w, about 10-95% w/w, about 15-90% w/w, about 20-90% w/w, about 30-90% w/w, about 40-85% w/w, about 50-80% w/w, about 60-70% w/w, about 70-90% w/w, or about 80-90% w/w.

A preparation of an active enamel substance for use according to the invention may also contain a mixture of proteins with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

As discussed above the low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenin, amelin, tuftelin, etc. with molecular weights (as measured in vitro with SDS-PAGE) below about 60,000 daltons but proteins having a molecular weight above 60,000 daltons have also promising properties as candidates for wound healing, anti-bacterial and/or anti-inflammatory agents.

Accordingly, it is contemplated that the active enamel substance for use according to the invention has a molecular weight of up to about 40,000 such as, e.g. a molecular weight of between about 5,000 and about 25,000.

Within the scope of the present invention are also peptides as described in WO 97/02730, i.e. peptides which comprise at least one sequence element selected from the group consisting of the tetrapeptides DGEA (Asp-Gly-Glu-Ala) (SEQ ID NO: 1), VTKG (Val-Thr-Lys-Gly) (SEQ ID NO: 2), EKGE (Glu-Lys-Gly-Glu) (SEQ ID NO: 3) and DKGE (Asp-Lys-Gly-Glu) (SEQ ID NO: 4) and which further comprise an amino acid sequence from which a consecutive string of 20 amino acids is identical to a degree of at least 80% with a string of amino acids having the same length selected from the group consisting of the amino acid sequence shown in SEQ ID NO:1 and a sequence consisting of amino acids 1 to 103 of SEQ ID NO:1 and amino acids 6 to 324 of SEQ ID NO:2 shown in WO 97/02730.

By the term "sequence identity" is meant the identity in sequence of amino acids in the match with respect to identity and position of the amino acids of the peptides. A gap is counted as non-identity for one or more amino acids as appropriate.

Such peptides may comprise from 6 to 300 amino acids, e.g. at least 20 amino acids, at least 30 amino acids, such as at least 60 amino acids, at least 90 amino acids, at least 120 amino acids, at least 150 amino acids or at least 200 amino acids.

A method for the isolation of enamel matrix proteins involves extraction of the proteins and removal of calcium and phosphate ions from solubilized hydroxyapatite by a suitable method, e.g. gel filtration, dialysis or ultrafiltration (see e.g. Janson, J-C & Rydén, L. (Eds.), Protein purification, VCH Publishers 1989 and Harris, ELV & Angal, S., Protein purification methods—A practical approach, IRL Press, Oxford 1990).

A typical lyophilized protein preparation may mainly or exclusively up to 70-90% contain amelogenins with a molecular weight (MW) between 40,000 and 5,000 daltons, the 10-30% being made up of smaller peptides, salts and residual water. The main protein bands are at 20 kDa, 12-14 kDa and around 5 kDa.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as amelin, tuftelin or proteolytic enzymes normally found in enamel matrix, can be added and carried by the amelogenin aggregate.

As an alternative source of the enamel matrix derivatives or proteins one may also use generally applicable synthetic routes well-known for a person skilled in the art or use cultivated cells or bacteria modified by recombinant DNA-techniques (see, e.g., Sambrook, J. et al.: Molecular Cloning, Cold Spring Harbor Laboratory Press, 1989).

Physico-Chemical Properties of Enamel Matrix, Enamel Matrix Derivatives and Enamel Matrix Proteins In general the enamel matrix, enamel matrix derivatives and enamel matrix proteins are hydrophobic substances, i.e. less soluble in water especially at increased temperatures. In general, these proteins are soluble at non-physiological pH values and at a low temperature such as about 4-20° C., while they will aggregate and precipitate at body temperature (35-37° C.) and neutral pH.

At least a part of the active enamel substance may be in the form of aggregates or is capable of forming aggregates after application in vivo. The particle size of the aggregates is in a range of from about 20 nm to about 1 µm.

It is contemplated that the solubility properties of the active enamel substance are of importance in connection with the prophylactic and therapeutic activity of the substance. When a composition containing the active enamel substance is administered to e.g. a human, the proteinaceous substances will precipitate due to the pH normally prevailing under physiological conditions. Thus, a layer of active enamel substance is formed at the application site and this layer (which also may be a molecular layer in those cases where aggregates have been formed) is difficult to rinse off under physiological conditions. Furthermore, due to the substances bioadhesive properties (see below) the precipitated layer is firmly bound to the tissue also at the margin between the precipitated layer and the tissue. The proteinaceous layer thus covers the tissue onto which the active enamel substance or compositions thereof have been applied and the active enamel substances are maintained in situ for a prolonged period of time, i.e. it is not necessary to administer the active enamel substance(s) with short intervals. Furthermore, the layer formed in situ can almost be compared to an occlusive dressing, i.e. the layer formed protects the tissue onto which the layer is formed from the surroundings.

In order to enable a proteinaceous layer to be formed in situ after application it may be advantageous to incorporate a suitable buffer substance in a pharmaceutical composition of the active enamel substance; the purpose of such a buffer substance could be to avoid the dissolution of the active enamel substance at the application site.

The active enamel substance has also been observed (by the present inventors) to possess bioadhesive properties, i.e. it has an ability to adhere to skin or mucosal surfaces. These properties are most valuable in connection with a therapeutic and/or prophylactic treatment at least for the following reasons:

the prophylactically and/or therapeutically active substance(s) can be maintained at the application site for a prolonged period of time (i.e. i) the administration frequency can be reduced, ii) a controlled release effect of the active substance is obtainable and/or iii) a local treatment at the application site is improved)

the active enamel substance may in itself be suitable as a vehicle for other prophylactically or therapeutically active substances because a vehicle containing the active enamel substance can be formulated as a bioadhesive vehicle (i.e. a novel bioadhesive drug delivery system based on the bioadhesive properties of the active enamel substance).

Pharmaceutical Compositions

For the administration to an individual (an animal or a human) the active enamel substance and/or a preparation thereof are preferably formulated into a pharmaceutical composition containing the active enamel substance and, optionally, one or more pharmaceutically acceptable excipients.

The compositions may be in form of, e.g., solid, semi-solid or fluid compositions such as, e.g., bioabsorbable patches, drenches, dressings, hydrogel dressings, hydrocolloid dressings, films, foams, sheets, bandages, plasters, delivery devices, implants, powders, granules, granulates, capsules, agarose or chitosan beads, tablets, pills, pellets, microcapsules, microspheres, nanoparticles, sprays, aerosols, inhalation devices, gels, hydrogels, pastes, ointments, creams, soaps, suppositories, vagitories, solutions, dispersions, suspensions, emulsions, mixtures, lotions, enemas, kits containing e.g. two separate containers, wherein the first one of the containers contains the active enamel substance e.g. in powder or freeze-dried form optionally admixed with other active drug substance(s) and/or pharmaceutically acceptable excipients and the second container containing a suitable medium intended to be added to the first container before use in order to obtain a ready-to-use composition;

and in other suitable forms such as, e.g., implants or coating of implants or in a form suitable for use in connection with implantation or transplantation.

Compositions for application to the skin or to the mucosa are considered most important in connection with the present invention. Thus, a composition comprising the active enamel substance to be administered may be adapted for administration by any suitable route, for example by topical (dermal), oral, buccal, nasal, aural, rectal or vaginal administration, or by administration to a body cavity such as, e.g., the oral, gastrointestinal, lung or abdominal cavity. Furthermore, a composition may be adapted to administration in connection with surgery, e.g. in connection with excision of tumours or neoplastic tissue or in conjunction with radiation therapy.

As mentioned above, a composition of the active enamel substance may be suitable for use during surgery, e.g. for topical application in the form of a gel, film or dry pellet, or as a rinsing solution or treatment with a paste or cream on tissue or surfaces.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

A pharmaceutical composition comprising an active enamel substance serves as a drug delivery system. In the present context the term "drug delivery system" denotes a pharmaceutical composition (a pharmaceutical formulation or a dosage form) which upon administration presents the active substance to the body of a human or an animal. Thus, the term "drug delivery system" embraces plain pharmaceutical compositions such as, e.g., creams, ointments, liquids, powders, tablets, etc. as well as more sophisticated formulations such as sprays, plasters, bandages, dressings, devices, etc.

Apart from the active enamel substance, a pharmaceutical composition for use according to the invention may comprise pharmaceutically acceptable excipients.

A pharmaceutically acceptable excipient is a substance which is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical composition is generally dependent on which kind of dosage form is chosen for use for a particular kind of wound. In the following are given examples of suitable pharmaceutically acceptable excipients for use in different kinds of compositions for use according to the invention.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

Compositions for Injection or Infusion

For systemic, non-topical administration, the composition comprising the active enamel substance may be in a form suited for systemic injection or infusion and may, as such, be formulated with sterile water or an isotonic saline or glucose solution. The composition may be sterilised by conventional sterilisation techniques which are well known in the art. The resulting aqueous solutions may be packaged for use or filtered under aseptic conditions and lyophilised, the lyophilised preparation being combined with the sterile aqueous solution prior to administration. The composition may contain pharmaceutically acceptable excipients as required to approximate physiological conditions, such as buffering agents, tonicity adjusting agents and the like, for instance sodium acetate, sodium lactate, sodium chloride, potassium chloride, calcium chloride, etc.

Topical Compositions

For application to the mucosa or the skin, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethylamine etc.

Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a surgical wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

Dressings and/or bandages are also important delivery systems for the active enamel substance. When dressings are used as dosage form, the active enamel substance may be admixed with the other ingredients before or during the manufacture of the dressing or the active enamel substance may in some way be coated onto the dressing e.g. by dipping the dressing in a solution or dispersion of the active enamel substance or by spraying a solution or dispersion of the active enamel substance onto the dressing. Alternatively, the active enamel substance may be applied in the form of a powder to the dressing. Dressings may be in the form of absorbent wound dressings for application to exuding wounds. Dressings may also be in the form of hydrogel dressings (e.g. cross-linked polymers such as, e.g. Intrasite® which contains carboxymethylcellulose, propylene glycol or polysaccharide, disaccharide and proteins) or in the form of occlusive dressings such as, e.g., alginates, chitosan, hydrophilic polyurethane film, collagen sheets, plates, powders, foams, or sponges, foams (e.g. polyurethane or silicone), hydrocolloids (e.g. carboxymethylcellulose, CMC), collagen and hyaluronic acid-based dressings including combinations thereof.

The compositions mentioned above for topical administration are most suitably for application directly to wounds or they may be suitable for application to or for introduction into relevant orifice(s) of the body, e.g. the rectal, urethral, vaginal, aural, nasal or oral orifices. The composition may simply be applied directly on the part to be treated such as, e.g., on the mucosa, or by any convenient route of administration.

Compositions which have proved to be of importance in connection with topical application are those which have thixotropic properties, i.e. the viscosity of the composition is affected e.g. by shaking or stirring so that the viscosity of the composition at the time of administration can be reduced and when the composition has been applied, the viscosity increases so that the composition remains at the application site.

Compositions for Application to Mucosa or Skin

Suitable compositions for use according to the invention may also be presented in the form of suspensions, emulsions or dispersions. Such compositions contains the active enamel substance in admixture with a dispersing or wetting agent, suspending agent, and/or one or more preservatives and other pharmaceutically acceptable excipients. Such compositions may also be suitable for use in the delivery of the active enamel substance to e.g. an intact or damaged mucosa such as the oral, buccal, nasal, rectal, or vaginal mucosa, or for administration to intact or damaged skin, or wounds.

Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate, etc.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and chitosans such as, e.g., sodium alginate, etc.

Suitable examples of preservatives for use in compositions according to the invention are the same as those mentioned above.

Rectal and/or Vaginal Compositions

For application to the rectal or vaginal mucosa, suitable compositions according to the invention include suppositories (emulsion or suspension type), enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives like, e.g., enhancers or surfactants may be incorporated.

Nasal or Pulmonary Compositions

For application to the nasal or pulmonal mucosa (as well as to the oral mucosa), sprays and aerosols for inhalation are suitable compositions according to the invention. In a typical composition, the active enamel substance is present in the form of a particulate formulation optionally dispersed in a suitable vehicle. The pharmaceutically acceptable vehicles and excipients and optionally other pharmaceutically acceptable materials present in the composition such as diluents, enhancers, flavouring agents, preservatives, etc. are all selected in accordance with conventional pharmaceutical practice in a manner understood by the persons skilled in the art of formulating pharmaceuticals.

Dosages of Enamel Matrix, Enamel Matrix Derivatives and Enamel Matrix Proteins

In a pharmaceutical composition for use according to the invention, an active enamel substance is generally present in a concentration ranging from about 0.01% to about 99.9% w/w. The amount of composition applied will normally result in an amount of total protein per $cm^2$ area of affected tissue corresponding to from about 0.01 $mg/cm^2$ to about 20 $mg/cm^2$ such as from about 0.1 $mg/cm^2$ to about 15 $mg/cm^2$.

The amount applied of the composition depends on the concentration of the active enamel substance in the composition and of the release rate of the active enamel substance from the composition, but is generally in a range corresponding to at the most about 15-20 $mg/cm^2$.

In those cases where the active enamel substance is administered in the form of a liquid composition, the concentration of the active enamel substance in the composition is in a range corresponding to from about 0.1 to about 50 mg/ml. Higher concentrations are in some cases desirable and can also be obtained such as a concentration of at least about 100 mg/ml.

The concentration of the active enamel substance in a pharmaceutical composition depends on the specific enamel substance, its potency, the severity of the disease to be prevented or treated, and the age and condition of the patient. Methods applicable to selecting relevant concentrations of the active enamel substance in the pharmaceutical composition are well known to a person skilled in the art and may be performed according to established guidelines for good clinical practice (GCP) or Investigational New Drug Exemption ("IND") regulations as described in e.g. International Standard ISO/DIS 14155 Clinical investigation of medical devices, 1994 and ICH (International Committee for Harmonisation): Harmonised tripartite guideline for good clinical practice, Brookwood Medical Publications, Ltd, Surrey, UK, 1996. A person skilled in the art would, by use of the methods described in standard textbooks, guidelines and regulations as described above as well as common general knowledge within the field, be able to select the exact dosage regimen to be implemented for any active enamel substance and/or selected other active substances and dosage form using merely routine experimentation procedures.

In accordance with the present invention, application of the active enamel substance at or on tumorous tissue may suitably be combined with other forms of tumour treatment, such as surgery, administration of chemotherapeutic agents and/or radiation therapy of affected tissue.

The invention is further described in the following examples which are not in any way intended to limit the scope of the invention as claimed.

BRIEF DESCRIPTION OF THE DRAWINGS

The invention is further described in the following with reference to the appended drawings, wherein.

Figure 1:
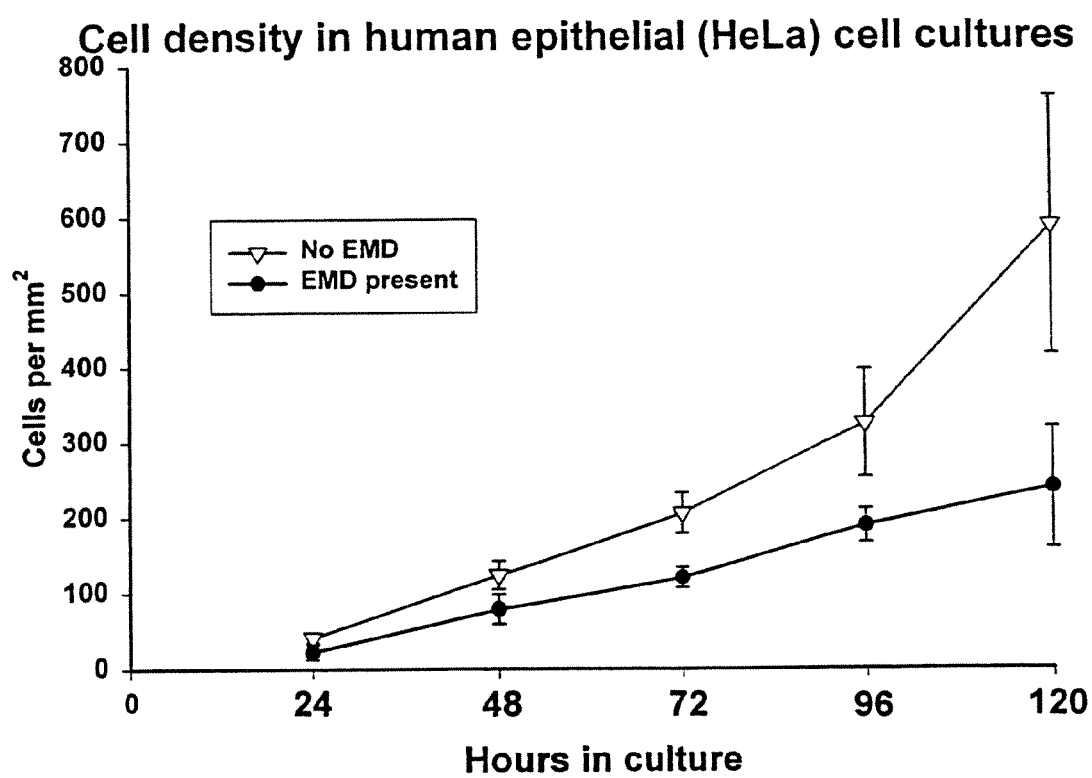
FIG. 1 is a graph showing the density of human epithelial (HeLa) cells grown in the presence and absence of EMD.

The present invention is further described in the following examples which are not in any way intended to limit the scope of the invention as claimed.

EXPERIMENTAL SECTION

Enamel Matrix Derivative, EMDOGAIN®, from BIORA AB, S-205 12 Malmö, Sweden containing 30 mg freeze-dried enamel matrix protein (in the following abbreviated to EMD) and 1 ml vehicle solution (Propylene Glycol Alginate), which are mixed prior to application, unless the protein and the vehicle are tested separately. The weight ratio is about 85/5/10 between the main protein peaks at 20, 14 and 5 kDa, respectively.

Example 1

Apoptosis in Guinea Pig Dental Epithelium

Tissue Preparation

Two guinea pigs of 200-250 g were anesthetized by carbon dioxide and decapitated. Bilateral maxilla and mandible were dissected and fixed with freshly prepared 4% paraformaldehyde in 0.1M phosphate buffer, pH 7.4, at 4° C. After fixation, the specimens were decalcified with neutral buffered 10% EDTA, dehydrated with graded ethanol, and embedded in paraffin. Sections (7 μm) were taken in the following directions: sagittal (mesio-distal) sections to obtain information about the changes in the enamel epithelium in association with the formation of the cementum pearls that are formed on the enamel surface, bucco-lingual sections to obtain information about changes in the epithelial root sheath that take place when dentin and cementum are formed at the apical end of the molars, horizontal sections to follow the distribution of the epithelium around the molars. These sections were used for immunohistochemical demonstration of the epithelial cells and their basal lamina as well as the possible occurrence of apoptosis. Some sections were stained with hematoxylin and eosin (H&E).

Immunohistochemical Detection of Laminin and Keratin

The sections were pretreated with 2% hydrogen peroxide to diminish endogenous peroxidase, incubated with 0.1% protease (Sigma, St, Louis, USA) for 15 min, and non-specific reaction was blocked with 4% normal goat serum (Dako, Copenhagen, Denmark). Then, they were incubated with rabbit anti-laminin antibody (1:1000, Dako, Copenhagen, Denmark) or mouse monoclonal anti-cytokeratin antibody (1:100, Boehringer-Mannheim, Germany) at 4° C. overnight, rinsed with TBS (50 mM Tris buffer saline, pH 7.4), incubated with goat anti-rabbit antibody with HRP (Dako, Copenhagen, Denmark) or goat anti-mouse antibody with HRP diluted to 1:100 (Dako, Copenhagen, Denmark) at room temperature for 60 min. The immunoreaction was visualized with 0.1% DAB (diamino benzidine), TBS were substituted for the primary antibodies in controls TUNEL procedure for the visualization of apoptosis The sections were deparaffinized with xylene, rehydrated with graded ethanol, and rinsed with PBS (phosphate-buffered saline, 50 mM sodium phosphate, 200 mM NaCl, pH 7.4). The sections were incubated with proteinase K (20 μg/ml in PBS, pH 7.4, Sigma, St. Louis, USA) for 15 min. at 37° C. to expose the DNA strands, and rinsed with PBS. Endogenous peroxidase was blocked by 2.0% hydrogen peroxide in PBS for 5 min. at room temperature, DIG labeled dUTP (deoxyuridine triphosphate) solution and TdT (terminal deoxynucleotidyl transferase) were mixed to make TUNEL mixture (Oncor, Gaithersburg, Md.). The sections were incubated with TUNEL mixture for 60 min. at 37° C. DIG labeled dUTP solution without TdT (terminal deoxynucleotidyl transferase) was used as negative control. After incubation, the specimens were rinsed with PBS and reacted with anti-Digoxigenin-peroxidase for 30 min. at room temperature. The reaction was visualized by 0.1% DAB with 0-02% hydrogen peroxide in PBS at room temperature. For positive controls, a mandible and a spleen of rats was observed in the same manner. Apoptotic cells were distributed in a part of incisal ameloblasts of transition-stage and a part of disintegrated enamel epithelium from FIRS in rat molars. Apoptotic cells were scattered in the spleen of a rat.

Results

The immunohistochemistry with antibodies against keratin showed the epithelial cells in all positions where they could be identified by means of ordinary light microscopy. In addition it was possible to distinguish epithelial cells in areas where cells of the enamel organ or the epithelial root sheath were mingled with mesenchymal cells of the dental follicle. Immunohistochemistry with antibodies against laminin showed that the epithelial structures were associated with a basement membrane in some areas and that a basement membrane was missing in others. The TUNEL method visualized apoptotic bodies in specific regions of the contiguously growing teeth.

It was observed that ameloblasts underwent apoptosis in early secretory stage, transition stage, maturation stage and reduced enamel epithelial stage. Apoptosis in maturation stage and reduced enamel epithelial stage appeared to be associated with the formation of cementum pearls. At the apical area of the cartilage-like cementum, the enamel organ which had a large stellate reticulum and lacked the distinct border of outer enamel epithelium was observed. Apoptosis of enamel epithelium was observed in the same portions as those of cementum pearls. Based on these results, it is considered likely that apoptosis plays an important part in the reduction, transformation, evacuation and migration of enamel epithelium, which is an important step for the formation of cementum during tooth development.

Example 2

Growth of Human Epithelial Cells in the Presence and Absence of EMD

Materials and Methods

Human epithelial cells (HeLa; a human cervical cancer cell line) were obtained from BioWhittaker, HeLa 07-229c, Lot #8c2720. The cells were grown in Modified Eagle's Medium supplemented with 10% fetal calf serum. EMD was supplied by surface coating culture dishes with a 0.1% EMD solution in 0.1% HAc, and by supplementing the culture medium with 100 μg EMD per ml of medium. HeLa cells cultured under similar conditions in the absence of EMD were used as controls. All experiments were initiated with 50,000 cells per ml of culture medium.

Results (a) HeLa cells were grown in cultures for 24, 48, 72, 96 and 120 hours. Cultures were then washed with PBS and cells were counted in the microscope using a fixed grid. Five different areas were counted in each of six parallel cultures at each timepoint. As appears from FIG. 1, HeLa cells show a marked decrease in cell density from 48 hours when grown in the presence of EMD.

Figure 2:
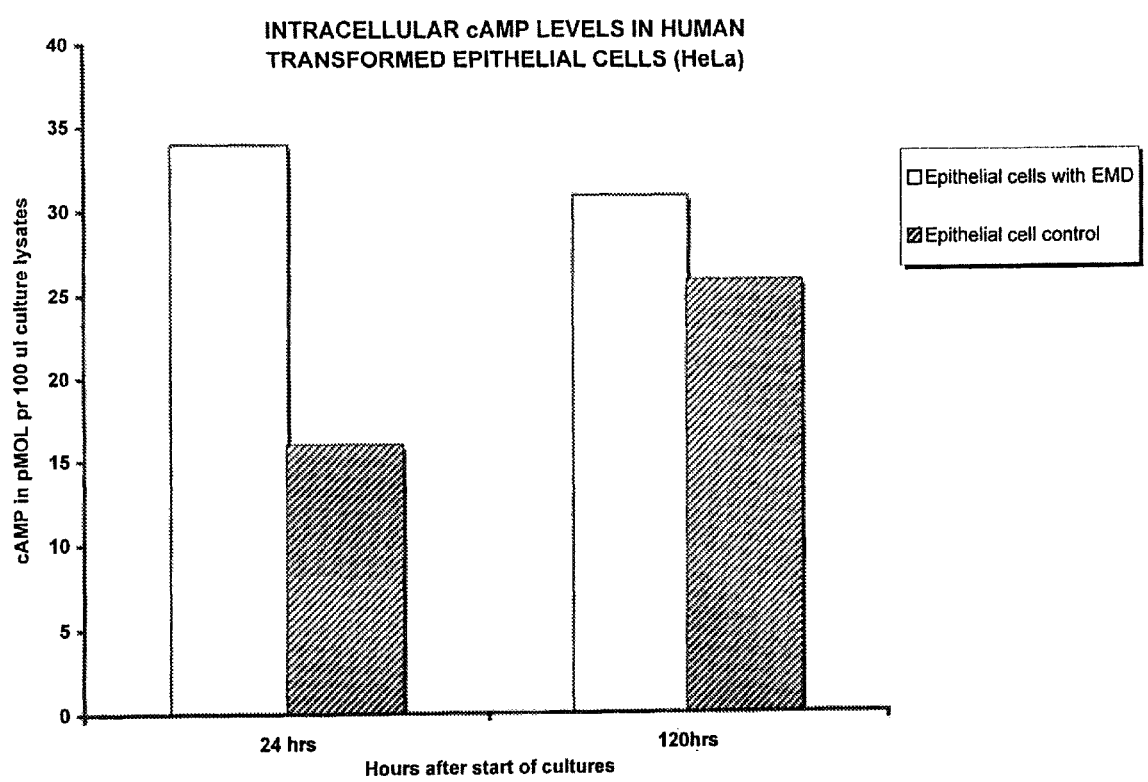
FIG. 2 is a graph showing the production of intracellular cAMP of HeLa cells grown in the presence or absence of EMD.

(b) HeLa cells were cultured for 24 or 120 hours, washed twice with PBS and centrifuged. 100 μl of cells from each culture (n=6 at each timepoint/experiment) were then lysed, and released intracellular cAMP was measured by competitive enzyme immunoassay (EIA) using an Amersham Pharmacia Biotech "Biotrak cAMP EIA" kit (Cat. No. RPN 225) in accordance with the manufacturer's instructions. Compared to controls, HeLa cells show a marked increase in intracellular cAMP after 24 hours of growth in the presence of EMD (FIG. 2). This increase could still be observed after 120 hours in culture. The increase in intracellular cAMP suggests that cells grown in the presence of EMD generate internal signal(s) that could be part of pathways for growth regulation and differentiation.

Figure 3:
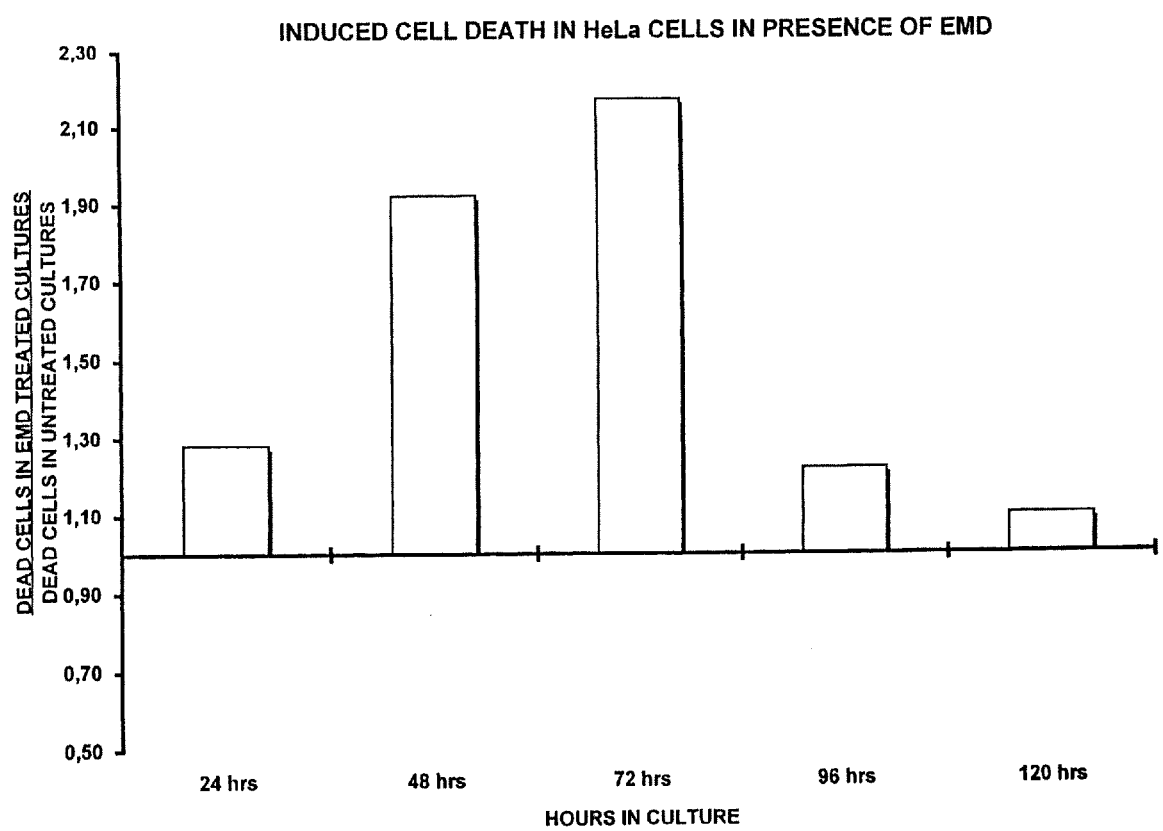
FIG. 3 is a graph showing induced cell death of HeLa cells grown in the presence of EMD compared to HeLa cells grown in the absence of EMD as measured by the level of apoptosis specific nucleic acid degradation products.

(c) HeLa cells were harvested from cultures at 24, 48, 72, 96 or 120 hours (n=5 at each timepoint/experiment), washed in PBS and centrifuged. 200 of cells were lysed, and the level of apoptosis specific nucleic acid degradation products (histone associated DNA fragments) was quantified by sandwich ELISA using a Boehringer Mannheim "Cell Death Detection ELISA" kit (Cat. No. 1 774 425) according to the manufacturer's instructions. The results are presented as the ratio between EMD treated cells and untreated cells. Hence values above 1 indicate induced cell death while values below 1 reflect prolonged cell survival. It appears from FIG. 3 that the HeLa cells show a marked increase in induced cell death when EMD is present in the cultures (values above 1), peaking at 72 hours after addition of EMD.

Based on these results, it is concluded that epithelial cell growth is poorer in the presence of EMD, and that the presence of EMD in the cultures increased programmed cell death more than two-fold.

Example 3

Growth of Human Cancer Cells in the Presence of EMD

Materials and Methods

Human cancer cells were obtained from cell culture banks derived from tumour tissues from patients undergoing cancer treatment at the Norwegian Cancer Hospital in Oslo, Norway. The cells were grown in Dulbecco's Modiefied Eagle's Medium supplemented with 10% fetal calf serum (osteosarcoma cells) or Eagle's Modified Eagle's Medium supplemented with 10% fetal calf serum (epithelial derived cells). EMD was supplied by surface coating culture dishes with a 0.5 mg/ml EMD solution in 0.01% HAc, and by supplementing the culture medium with 100 μg EMD per ml of medium. All experiments were initiated with 50,000 cells per ml of culture medium.

Results

Cells were harvested from the cultures at 72 and 120 hours (n=3×3 each time). The cells were washed in PBS and centrifuged, and 200 μl of cells from each sample were lysed and the level of apoptosis specific nucleic acid degradation products (histone associated DNA fragments) was quantified by sandwich ELISA using a Boehringer Mannheim "Cell Death Detection ELISA" kit (Cat. No. 1 774 425) according to the manufacturer's instructions. The results are presented as the ratio between EMD treated cells and untreated cells. Hence values above 1 indicate induced cell death while values below 1 reflect prolonged cell survival.

It appears from Table 1 below that human cancer cells show a marked increase (values above 1) in induced cell death in the presence of EMD in the cell cultures, peaking at 72 to 120 hours after addition of EMD.

TABLE 1

| Tissue of origin cell line | 72 hours after addition of EMD | 120 Hours after addition of EMD |
|---|---|---|
| Mammary glands | | |
| MCF-7 | 1.1 | 1.3 |
| SK-BR-3 | 1.1 | 1.2 |
| T47D | 1.3 | 1.2 |
| ZR35 | 2.1 | 1.8 |
| Osteosarcoma (bone) | | |
| OHS | 2.5 | 1.4 |
| Melanoma (skin) | | |
| LOX | 1.1 | 1.1 |
| FEMX-1 | 1.5 | 1.4 |
| Ovarian carcinoma | | |
| OVCAR | 3.5 | 2.5 |
| SK-OV-3 | 2.8 | 1.4 |
| Rhabdomyosarcoma (muscle) | | |
| RH-28 | 2.7 | 1.7 |

The invention claimed is:

1. A method of inducing apoptosis in an ovarian neoplasm comprising administering to a human or animal having ovarian cancer a therapeutically effective amount of a composition comprising a low molecular weight fraction of acetic acid extractable proteins from an enamel matrix.

2. The method of claim 1, wherein the low molecular weight fraction of acetic acid extractable proteins from an enamel matrix comprises main protein peaks having a molecular weight of 20 kDa, 12-14 kDa, and 5 kDa, as determined by SDS gel electrophoresis.

3. The method of claim 1, wherein the low molecular weight fraction of acetic acid extractable proteins from an enamel matrix mainly consists of amelogenin.

4. The method of claim 1, wherein the main protein peaks having a molecular weight of 20 kDa, 12-14 kDa, and 5 kDa as determined by SDS gel electrophoresis are present in a ratio, based on weight, of approximately 85/5/10, respectively.

5. The method of claim 1, wherein the enamel matrix is porcine enamel matrix.

6. The method of claim 1, wherein the ovarian neoplasm is an ectodermal neoplasm.

7. The method of claim 1 wherein the ovarian neoplasm is an epithelial neoplasm.

8. The method of claim 1, wherein the ovarian neoplasm is semimalignant and/or malignant.

9. The method of claim 1, wherein the composition is administered as a pharmaceutical composition.

10. The method of claim 9, wherein the pharmaceutical composition comprises a pharmaceutically acceptable excipient.

11. The method of claim 10, wherein the excipient is propylene glycol alginate.

12. The method of claim 10, wherein the excipient is hyaluronic acid or a salt derivative thereof.

13. The method of claim 1, wherein the composition is administered topically.

14. The method of claim 1, wherein the composition is administered in the range of about 0.1 mg/cm$^2$ to about 15 mg/cm$^2$.

15. The method of claim 1, wherein the composition is administered in the range of about 0.01 mg/cm$^2$ to about 20 mg/cm$^2$.

* * * * *